United States Patent [19]
Koepnick

[11] Patent Number: 5,496,339
[45] Date of Patent: Mar. 5, 1996

[54] UNIVERSAL AUTOMATED KERATECTOMY APPARATUS AND METHOD

[76] Inventor: Russell G. Koepnick, 2323 N. Central Ave., #1505, Phoenix, Ariz. 85004

[21] Appl. No.: 245,228

[22] Filed: May 17, 1994

[51] Int. Cl.⁶ .................................................. A61B 17/32
[52] U.S. Cl. .................................................. 606/166
[58] Field of Search ................................. 606/166, 167

[56] References Cited

U.S. PATENT DOCUMENTS

| | | | |
|---|---|---|---|
| 4,662,370 | 5/1987 | Hoffman et al. | 128/305 |
| 4,884,570 | 12/1989 | Krumeich et al. | 128/305 |
| 5,133,726 | 7/1992 | Ruiz et al. | 606/166 |
| 5,288,292 | 2/1994 | Giraud et al. | 606/166 |

Primary Examiner—Stephen C. Pellegrino
Assistant Examiner—W. Lewis
Attorney, Agent, or Firm—Donald J. Lenkszus

[57] ABSTRACT

A surgical device for altering the curvature of an eye includes a base which carries a transparent insert, a drive device, a knife edge coupled to the drive device and movable to a plane immediately adjacent the under surface of the transparent insert. The transparent insert includes a face having a surface portion shaped according to a predetermined correction. The base further includes a suction ring which forms a vacuum chamber with the eye. The suction ring is placed against the eye. Application of vacuum results in the cornea of the eye being urged into engagement with the shaped surface portion. Actuation of the drive device moves the knife edge whereby the cornea is cut. Only the knife edge traverses the insert.

50 Claims, 9 Drawing Sheets

UNIVERSAL AUTOMATED KERATECTOMY APPARATUS AND METHOD

BACKGROUND OF THE INVENTION

1. Fields of the Invention

The present invention relates generally to apparatus and methods for mechanically performing single or multiple pass keratectomy for the correction of myopia, hyperopia and astigmatism, and, more particularly, to a surgical device that slices off a corneal disk by electromechanically driving only a reciprocating knife over the eye.

2. Discussion of Background and Prior Art a. Eye Conditions

The treatable defective conditions of the optical system in the eye are well known. Myopia (nearsightedness) is a condition where the visual images come to focus in front of the retina of the eye resulting in defective vision of distant objects. Hyperopia (farsightedness) is a condition in which visual images come to focus behind the retina of the eye and vision is better for distant objects than for near objects. Astigmatism is a defect of an optical system (as a lens) in consequence of which rays from a point fail to meet in a focal point resulting in a blurred and imperfect image. In the human eye this defect of vision due to astigmatism of the refractive system of the eye is usually due to corneal irregularity.

b. Prior Solutions

(1). Corrective Glasses

For many years ophthalmologists and optometrists have routinely treated patients that had these visual defects by prescribing appropriate eye glasses and contact lens, and that practice is still widely practiced today. However, many people cannot afford glasses or contact lens, or find them to be a nuisance or a temporary solution.

(2). Surgical Solutions

Approximately thirty years ago ophthalmologists began to perform surgical procedures on the human cornea to correct these visual problems. The practice has come to be known as refractive surgery, and its purpose has been to surgically alter the cornea in order to change the refractive power of the cornea and thus eliminate the need for eye glasses or contact lens.

(a). Barraquer Movable Plate Microkeratome

One of the first procedures for refractive surgery was the Barraquer microkeratome which placed against the cornea a flat applanate surface supported with the knife (as in a plane) guided by spaced apart dovetailed guides which formed rails on a suction ring applied to the sclera and then manually passed across the cornea at an angle thereto a power driven reciprocating knife edge in a guideway to remove a round lamellar (sides parallel to the surface of the cornea) disk. The thickness of the cut disk was controlled by the thickness of a spacer plate (numerous plates for various thicknesses) and the cut disk rolled up into a groove between the spacer plate and the block carrying the knife as the cut was made. The cut disk was then frozen, lathed and replaced. The procedure was known as keratomileusis. This complex device required extremely high surgical skills and the device had limited applications.

Multi-Pass Keratomes

More recent developments utilized multiple lamellar cuts of the cornea—a first cut followed by a second smaller cut and then sewing the first disk back on—known as keratomileusis in-situ which eliminated the freezing process and overcame many of the problems of the keratomileusis procedure. However, mechanical instruments known as keratomes still lacked precision, predictability and the ability to make smooth corneal cuts.

Adjustable Plate Keratomes With Micrometers

More recent developments of microkeratomes, for example, Giraud et al U.S. Pat. No. 5,288,292 and Giraud et al co-pending application Ser. No. 07/775,178, filed Oct. 11, 1991, applicant being a co-inventor thereof in each case, have replaced Barraquer's multiple spacer plates for controlling the thickness of the cut with a single adjustable plate which controls the space between the plate and knife edge and, hence, the slice thickness. Micrometers have even been placed on the microkeratome to precisely control the thickness. While these advances have proved that precise smooth cutting instruments could be manufactured, nevertheless, the complicated procedures have prevented even skilled ophthalmic surgeons from obtaining, repeatable, precise and predictable results. Moreover, no single instrument is applicable to all defective sight conditions nor can the procedures be easily carried out in a doctor's office.

(b). Radial Keratotomy

Another procedure known as radial keratotomy evolved and is used extensively for the correction of low to medium myopia and astigmatism. The procedure involves changing the shape of the cornea by making four, eight, or sixteen deep corneal cuts (80–90% of corneal thickness) extending out from a central optical zone of about 3 mm diameter. While many patients report satisfactory results, others are bothered by regression and many experience a starburst effect from the reflection of light at nighttime when the pupil is dilated larger than 3 mm. The scars from the deep corneal incisions apparently reflect light at night time. Radial keratotomy is usually limited to about 8 diopters of refractive correction. While the procedure is done routinely and in large numbers around the world, the effectiveness of the procedure still is a subject of sometimes heated debate.

(c). Eximer Lasers

More recently eximer lasers have been touted as the wave of the future for corneal sculpturing for correction of myopia and astigmatism. The eximer laser ablates (removes by vaporization) the cornea in a manner that results in removing a lenticular (sides not parallel to the surface of the cornea) disk from the cornea with a diameter of about 5–6 mm. The procedure requires that the epithelium (thin outer layer of the eye) be scrapped off and then the eximer laser ablates the cornea in a series of stepped ablations which leave a less than smooth surface on the corneal bed. The procedure subjects patients to substantial pain for a few days and obstructed vision for months. The use of eximer lasers to remove superficial irregularities of the cornea has met with mixed success due to ablation induced hyperopic shifts of corneal refraction. However, the big obstacles to widespread use of the eximer laser are the lack of FDA approval, unpredictability, imprecision, and the high cost of the equipment and maintenance.

(d). Keratome With Stationary Custom Ground Inserts

Figures 1, 2, 2A:
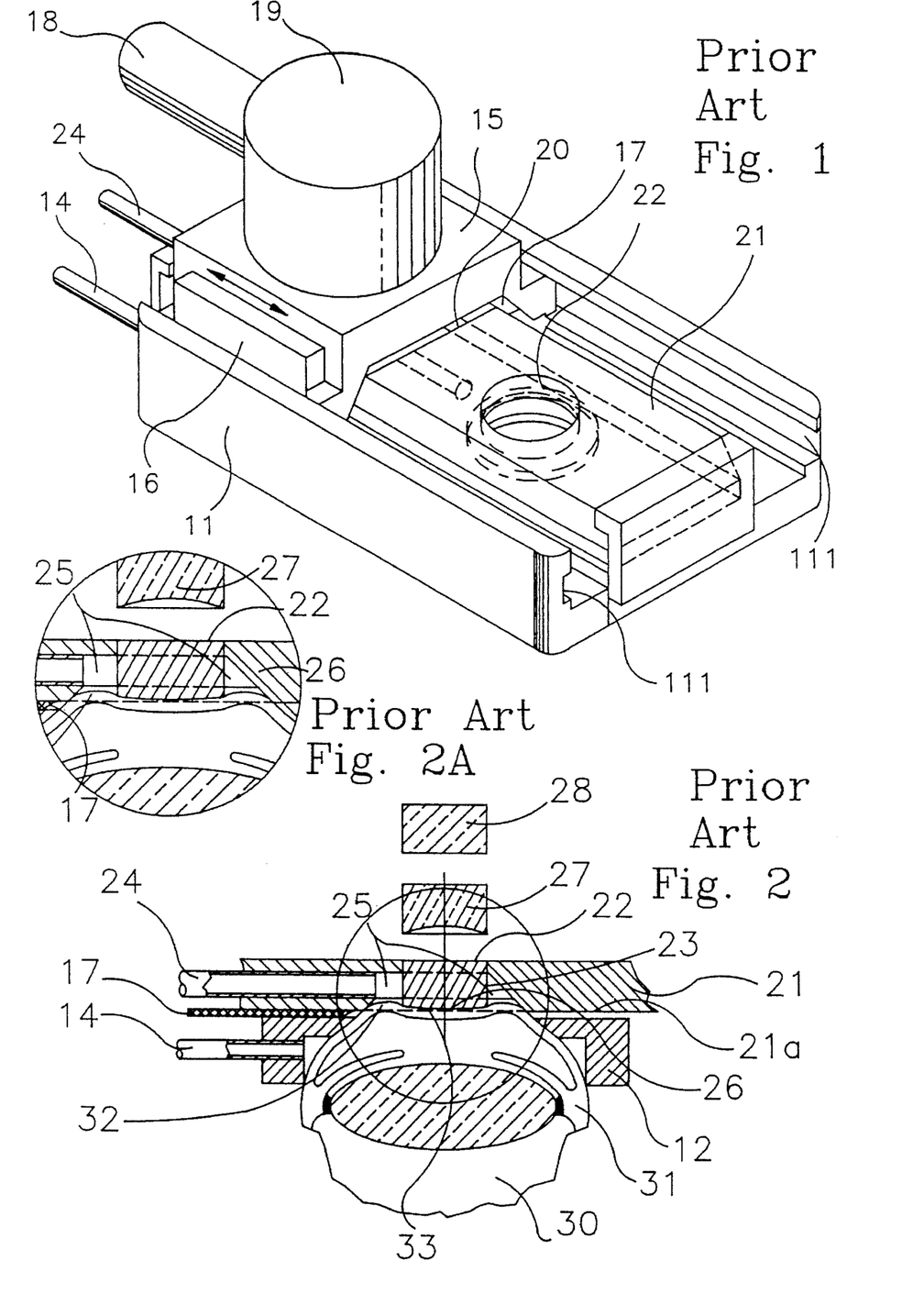
FIG. 1 is a perspective view of a prior art keratome shown schematically in FIG. 2.
FIG. 2 is a schematic in partial section of FIG. 1.
FIG. 2A is a blow-up of the circled portion of FIG. 2.

In a recent development of Hoffman (U.S. Pat. No. 4,662,370), shown herein as FIGS. 1, 2 and 2A, the adjustable movable plate of the earlier devices has been completely replaced by a fixed plate 21 with vacuum 24 holding in bore 23 a tapered, vacuum tight insert 22 the face 26 of which has been custom ground to a predetermined convex 22, concave 27 or planar 28 correction. A base plate 11 includes slide bearings 111 of support 15 for holder 16. A suction ring 12 with its separate vacuum 14 supports the device on the sclera 31 of the eye 30 and also supports the plate 21 which is stationary relative to the knife 17 reciprocating in an air gap between surface 21a and the top of the suction ring and supported in holder 16 under driver 18,19. Vacuum 24 and annulus 25 assist in holding the cornea 32 against the insert corrected face 26 and the cut of the cornea is made in cutting plane 33 beginning at the outboard edge of annulus 25 (FIG. 2A) by manually moving the blade and its related superstructure across the eye.

However, Hoffman's solution presents numerous problems including beginning the cut of the cornea outside of the correction zone, passing superstructure over the cornea blocking the surgeons view during the cut, the complexity and cost of multiple vacuums and the absence of any automated advance to provide more predictable and repeatable results. While an automated advance was subsequently developed by Ruiz (U.S. Pat. No. 5,133,726), it was only applicable to the old movable plate type keratomes.

(e). Contact Lens Experiments

Applicant is aware of one ophthalmic surgeon who attempted to place a thin molded material on the cornea and then simultaneously cut the material and the cornea with a movable plate keratome designed to make a lamellar cut. The results were intended to make a lenticular cut of the cornea. The cutting of the material along with the cornea did not work properly. However, subsequent tests were made using an ordinary soft contact lens with a ground optical correction placed upon the cornea. The successful result was a lenticular cut of the cornea using an adjustable, movable plate, lamellar cutting keratome. While this method is possible, it is impractical due to the difficulty in placing the contact lens in the exact desired place on the cornea and cutting the lens and cornea without having the lens move relative to the cornea during the operation.

Thus there remains a long felt need for a smooth cutting keratome that can be used for all defective vision corrections including those requiring irregular cuts, cuts only under a prescribed, predetermined corrected surface, provides automated advance without blocking the surgeon's vision during the cut and is so simple in its construction and use that a technician could perform the surgery in a doctor's office with a high degree of success.

Accordingly, it is an object of the present invention to provide an ophthalmic procedure and surgical instrument which makes a single cut of the cornea in precisely the correct position, either concave, convex, or irregular, in order to make the exact refractive change desired for the respective visual abnormalities of myopia, hyperopia, and astigmatism.

It is the further object of the present invention to leave a smooth corneal bed with no indications of the lateral movement of the cutting blade or peaks and valleys when photographed by scanning electron microscopy under a very high magnification.

It is the further object of the present invention that the procedure and instrumentation be extremely user friendly and useable effectively by surgeons possessing only minimal skills.

It is the further object of the present invention to provide one instrument that will correct the entire range of myopia, hyperopia, and astigmatism and which can also provide a bifocal correction of the cornea for those patients who suffer from presbyopia (a form of hyperopia).

It is the further object of the present invention that if for some reason the desired refractive correction was not correct, that the surgery may be reversed.

SUMMARY OF THE INVENTION

Set forth below is a brief summary of the invention in order to achieve the forgoing and other benefits and advantages in accordance with the purposes of the present invention as embodied and broadly described herein.

One aspect of the invention is in a surgical device for altering a curvature of an eye by cutting off a corneal disk with a slidable, reciprocable knife edge which is movable in a plane adjacent an insert which is stationary relative to the eye, the insert having a face having a surface portion shaped according to a predetermined correction, and a suction ring adapted to be positioned and held against the sclera of the eye with the corrected surface portion of the insert touching the cornea of the eye. In accordance with the principles of the invention, the knife edge is movable transverse to the eye to cut only the corneal tissue under the insert, and, in particular, only the corneal tissue under the corrected surface portion of the insert.

A further feature of this aspect of the invention is the insert is transparent, and has a crosshair image for aligning the insert with the cornea prior to cutting.

A second aspect of the invention is the insert holder, insert and suction ring form an assembly in which the suction ring and a sclera of an eye when received therein form the single and sole annular vacuum chamber in the entire assembly.

A third aspect of the invention is that the assembly has a first insert holder adjacent the suction ring, a second insert holder adjacent the first insert holder, and the insert is receivable and holdable between the first and second holders.

A further feature of this aspect of the invention is a plurality of registrators indexing the corrected surface to the holder and affixing the insert to the holder whereby the corrected surface may be aligned with a predetermined optical portion of the eye when the latter is received in the suction ring.

A further feature of this aspect of the invention is the insert holder is adapted to removably receive the insert, and the suction ring is removably coupled to the insert holder for inserting and removing the insert therebetween, or for removing the cut disk from between the knife and the corrected surface of the insert, with the knife in the retracted position.

A further feature of this aspect of the invention is the removable coupling is a hinge connecting the suction ring and the insert holder which are releasably latchable by a clasp.

A fourth aspect of the present invention is the knife is slidable in a knife guide recess in a plane in a suction ring portion parallel and adjacent to the face of the insert with the knife extending in the plane sufficiently in advance of a mechanism which drives and advances the knife whereby the only portion of the device which passes over the eye during the cutting operation is the knife.

A further feature of this aspect of the invention is a bracket adapted to be attached to a surface of the holder away from the suction ring and to receive an electromechanical advancer for moving the knife between the retracted and advanced positions at a predetermined rate.

A fifth aspect of the invention is the knife edge is electro-mechanically advanceable at a predetermined rate and slidably, reciprocable in the plane parallel and adjacent to the insert face.

A sixth aspect of the invention is a cam block fixedly mounted relative to the knife on a support and having a T-shaped slot with a T-shaped cam slidably, reciprocably mounted therein both mutually perpendicular to an axis of rotation of a drive shaft and a plane of reciprocation of the knife, the T-cam having a cam lug at one end received in a cam lug opening of the knife and an eccentric extension on the shaft slidably and rotatably received within a cam slot in the T-cam, whereby rotation of the shaft is translated to reciprocation of the knife edge.

Thus, the invention has significant advantages over prior technologies.

The invention is an improvement over other mechanical microkeratomes because of its extreme precision, its improved smoothness of the corneal cut, its additional safety features, its ability to make desired refractive corrections with a single pass as opposed to multiple passes, its ability to make lenticular, lameliar, planar and irregular cuts over a wide range of refractive corrections and its extreme ease of use.

The invention is an improvement over eximer laser because of its elimination of corneal haze, it's intrinsic safety as opposed to the unknown side effects of laser ablations, its ability to perform superficial keratectomy without creating hyperopic shifts and its fractional cost (approximately 10%) of the acquisition and maintenance of an eximer laser system.

The invention is an improvement over radial keratectomy because of its reduced patient trauma, its elimination of the starburst effect and its substantially reduced potential of penetrating into the anterior chamber.

Additionally, the invention has the major advantage over mechanical keratomes, eximer lasers and radial keratectomy because of its reversibility which can be accomplished by simply replacing the excised corneal disk or by excising another disk from a donor cornea using the same insert as used for the original operation.

DETAILED DESCRIPTION OF THE PREFERRED EMBODIMENT

General Overview

Referring to FIGS. 3–8, in the present invention the change in the corneal surface after a single pass keratectomy using the surgical device of the present invention will be determined by an optical correction ground into a custom made insert based upon the doctor's prescription. The prescription is similar to the prescription a doctor might give to an optical laboratory for the purpose of grinding lenses for eye glasses or for contact lenses. Instead, applicant grinds the optical prescription into a flat face 47 of an insert 48. The insert is then inserted into applicant's instrument 110 which uses the ground corrected portion 46 of the insert face 47 as a guide for cutting off an equivalent cornea portion 56 of the eye 50 thereby altering the curvature of the cornea 51 precisely the prescribed amount.

Figures 3, 4:
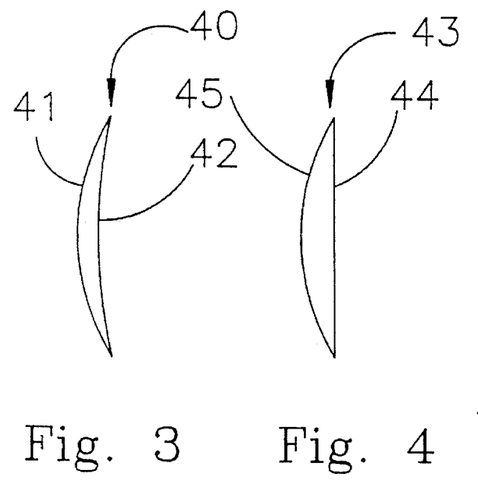
FIG. 3 is a schematic section of a lenticular corneal disk cut.
FIG. 4 is the mathematical equivalent of FIG. 3 in plano-convex form.
Figure 5:
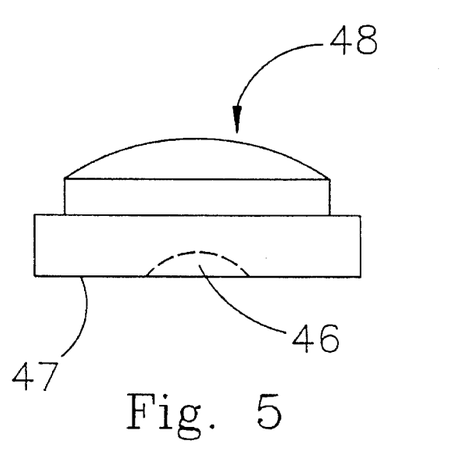
FIG. 5 is an insert of the present invention with a concave correction ground into its bottom surface.
Figures 6, 7:
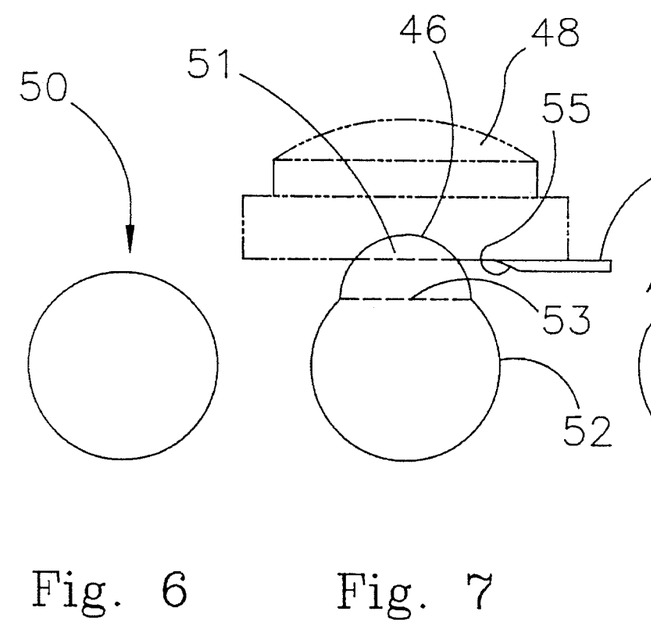
FIG. 6 is a schematic of the cornea of the eye before vacuum is applied.
FIG. 7 is a schematic of the cornea with the vacuum applied.

For example, as seen in FIG. 3, assuming a particular case of a patient wearing a contact lens 40 into the under surface 42 of which had been ground a particular prescribed correction, each of the two surfaces 41, 42 in this case being a positive meniscus (crescent) in shape. In the present invention, this correction is readily surgically placed permanently into the patient's cornea 51. This prescription is converted mathematically to the optical equivalent 43 seen in FIG. 4 having planar 44 and convex 45 sides which, as seen in FIG. 5, is then ground 46 into the flat face 47 of the insert 48 of the present invention which, as described below, fits into the cutting instrument 110. As seen in FIG. 7 (and as explained below in connection with FIGS. 26, 28) the optically ground concave correction portion 46 of flat face 47 of the insert 48 will, in the present invention, after proper adjustment of the vacuum, be the only portion of the face 47 to come into direct contact with the cornea 51 at the time the cut is made.

The instrument 140 is affixed to the sclera 52 of the eye 50 by a suction ring 71 (FIG. 26) on the line 53 (FIG. 7) with a partial vacuum applied. As seen schematically in FIG. 7, when the partial vacuum is applied to the sclera 52 and adjusted to the proper level, a downward force is applied to cornea 51 raising the innerocular pressure in the eye 50 and forcing the eye to bulge outwardly causing the cornea 51 to fill the optically ground concave depression 46 of the insert 48 (in the example under discussion). The amount of cornea 51 filling the depression 46 in the ground insert 48 is rapidly but smoothly excised by a high speed oscillating knife 54 with a concave 55 knife edge 81 (FIG. 19) that is electro-mechanically advanced across the eye at a predetermined rate in a plane parallel and adjacent to the flat face 47 of the insert 48. Only the amount of the cornea 51 that is forced into the concave recess (in this example) of the insert 48 will be cut from the cornea.

Figure 8:
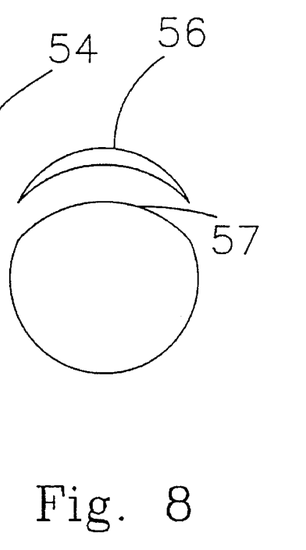
FIG. 8 is a schematic of the cornea after the cut with the vacuum off.
Figure 9:
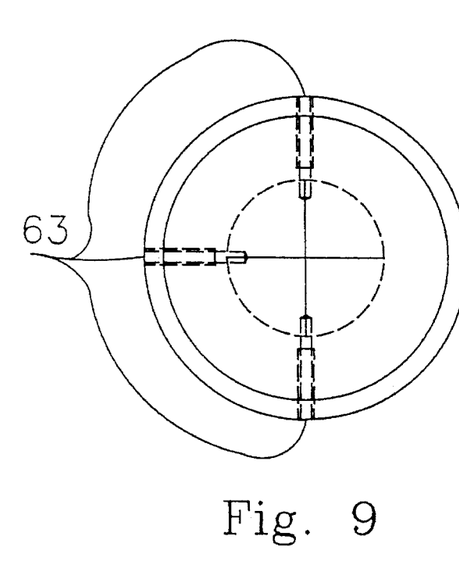
FIG. 9 is a top plan view of FIG. 12.
Figure 10:
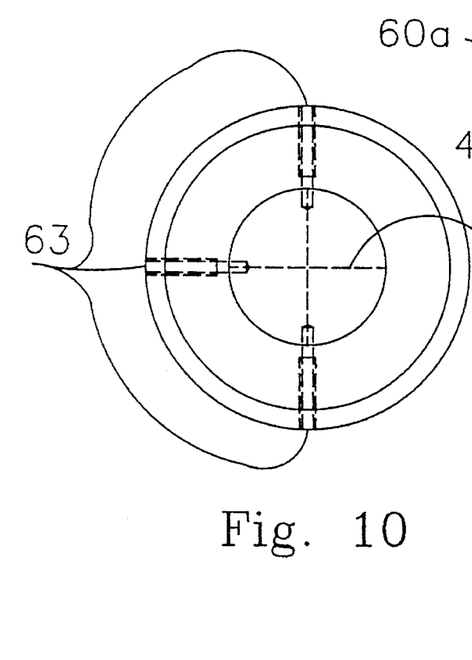
FIG. 10 is a bottom plan view of FIG. 12.

As seen in FIG. 8, when the vacuum 75, 132 is released the cornea 51 will return to its normal shape less the disk portion 56 excised by the cut. In the example just described the disk 56 will be the removal of a lenticular cut of the required refraction so that the remaining cornea 57 has precisely the proper refractive power for emmetropia (normal vision).

Additional examples can be provided whereby a convex, planar or irregular correction may be ground into the flat face 47 of the insert 48 to provide corresponding corrective cuts in the cornea.

The precision of the procedure and the instrument rests largely on the ability of existing grinding techniques and computer technology that allow grinding the recess of the insert 48 to within two tenths of a micron. Irregular corrections for such defects as astigmatism may be laser cut into the insert 48. The refractive correction for any degree of myopia, hyperopia, or astigmatism can therefore be ground precisely and predictably into an insert and applied to the cornea with the present invention.

The Optical Insert

Shown in FIGS. 9–13 is an optical insert of the present invention with flat face 47 and concave correction 46 ground therein to correct for hyperopia. The outer walls 60,61 are cylindrical with wall 61 of reduced diameter providing a shoulder 62. Registrators 63, which are tapped holes in the insert 48 receiving screws (not shown), index the corrected surface 46 to the first holder 70 and are used to affix the insert to the first holder 70 whereby the corrected surface may be aligned with a predetermined optical portion of the eye when the latter is received in the suction ring 71. Equivalent registrators are slots and lugs. Alignment is achieved using crosshairs 64 which allows the surgeon to look through the insert to align the crosshairs with the optical center of the eye after which the vacuum is applied. Insert 48 is transparent and is preferably made of an acrylic plastic such as the well known PMMA. Equivalent materials include any materials used for the manufacture of eye glasses or hard contact lens.

Figure 11:
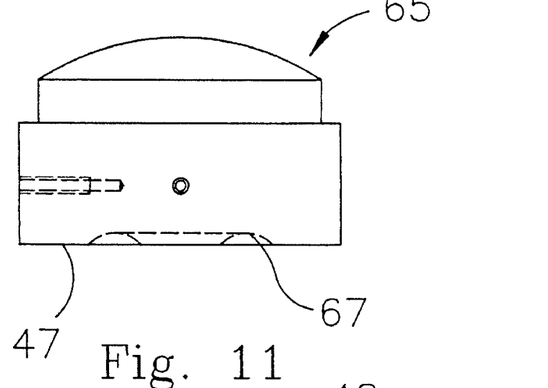
FIG. 11 is an elevation view of an optical insert of the present invention with a convex correction.
Figure 12:
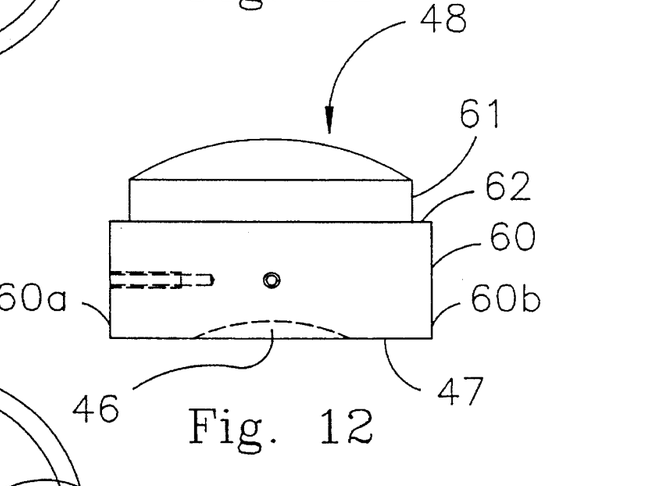
FIG. 12 is an elevation view of an optical insert of the present invention with a concave correction.
Figure 13:
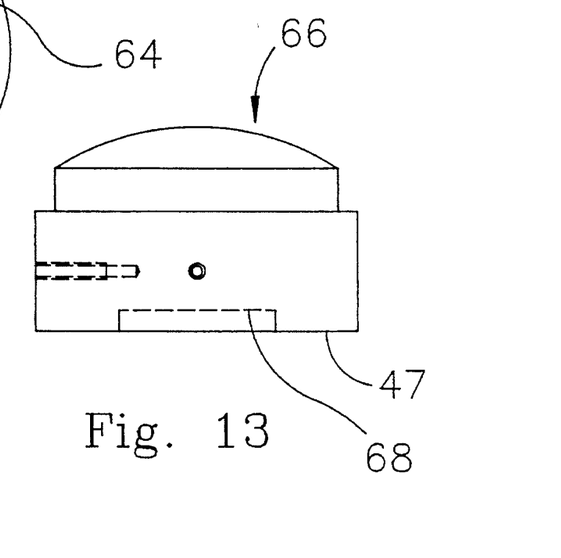
FIG. 13 is an elevation view of an optical insert of the present invention with a planar correction.

Inserts 65,66 have convex correction 67 and planar correction 68 ground into flat face 47, respectively. Correction 67 will produce a disk which is of reduced thickness centrally to correct myopia and correction 68 will produce an essentially lamellar cut disk of any desired thickness or diameter. Irregular cuts are possible to correct for astigmatism, and other defects.

The Holder Assembly 140

1. The Suction Ring and Blade Guide

Figure 14:
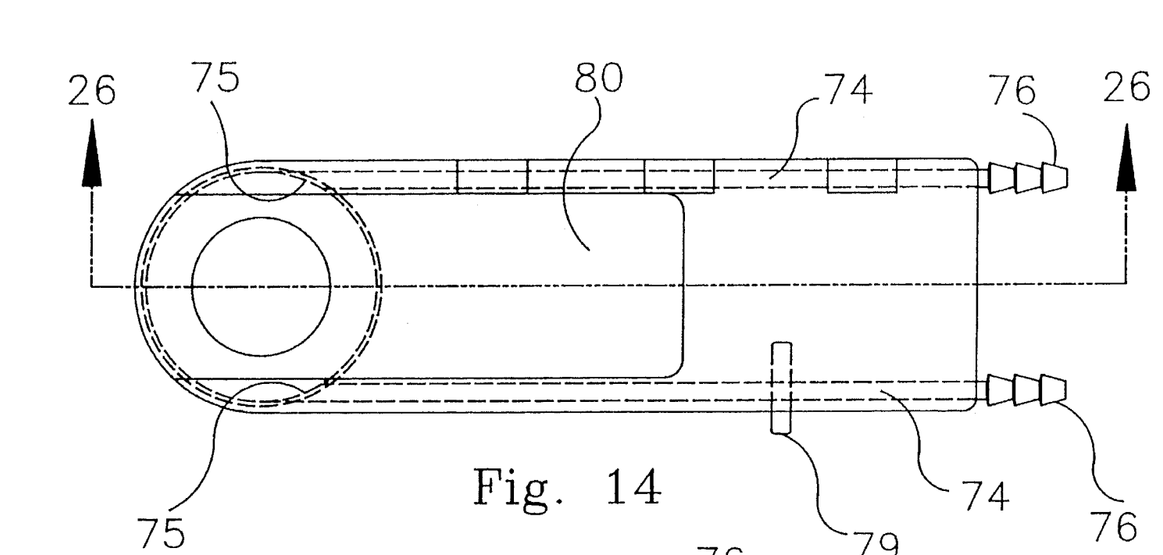
FIG. 14 is a top view of FIG. 15.
Figure 15:
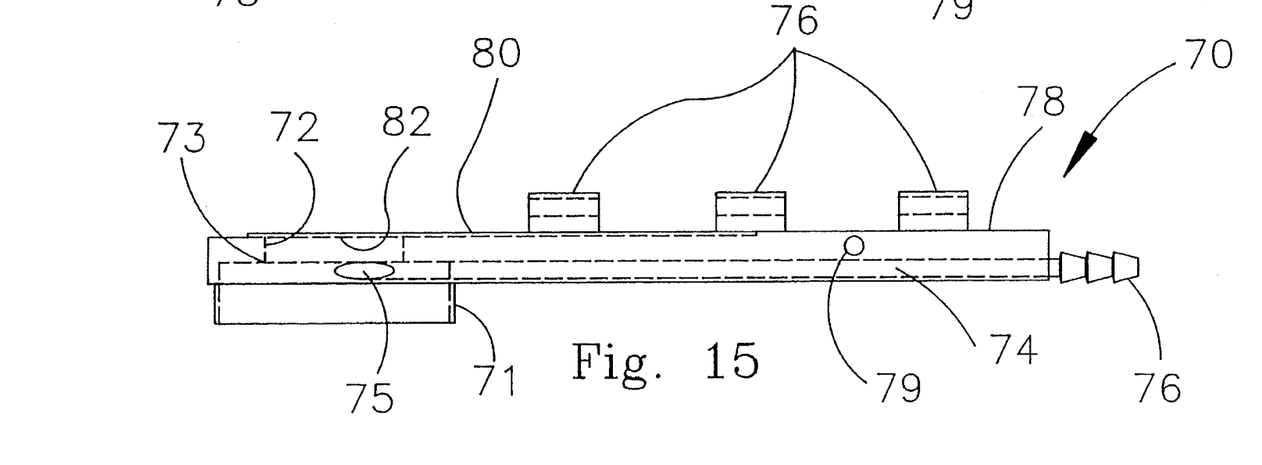
FIG. 15 is a front elevation view of the suction ring and blade guide of the present invention.
Figure 16:
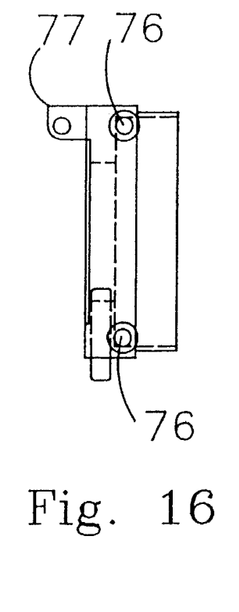
FIG. 16 is a right side view of FIG. 14.

Shown in FIGS. 14–16 is the suction ring and blade guide 70 having a suction ring 71 of inner diameter smaller than inner diameter 72 forming a square corner or shoulder 73 for exerting solely a downward force to the sclera whereby the eye will react to the downward force to bulge outwardly and place a cornea portion 51 completely against the shaped surface portion 46, 67, 68 of the insert 48, 65, 66 for the cutting operation. Also note that the inside diameter 72 of the suction ring 71 adjacent the insert 48 is smaller than the outside diameter 60 of insert 48 adjacent the suction ring 71 and inside diameter 72. Thus, in the present invention, the knife 54 will cut only under the insert 48. Vacuum passages 74 in the outboard ends of member 70 exit at ports 75 in ring 71 at one end and in barb 76 at the other end. Bored hinge posts 77 extend above the upper surface 78 of member 70 and are rotatably received within recesses 96 in the first insert holder 90 to form an internal hinge coupling the suction ring 71 to the first holder 90. Equivalent coupling means include a tongue and groove connection. Post 79 receives clasp 97 to latch the ring 71 to the holder 90. Equivalent latch means include a slide pin in a recess.

As seen in FIGS. 14, 15, recess 80 in the upper surface of member 70 forms a flat blade guide for the flat knife 54. The knife guide recess 80 is in a plane in the suction ring portion parallel and adjacent to the face 47 of the insert 48, as more fully described below, and the knife 54 is slidable (right to left in FIG. 14) and slidably reciprocable (top to bottom in FIG. 14) in the recess 54.

2. The Knife

Figure 17:
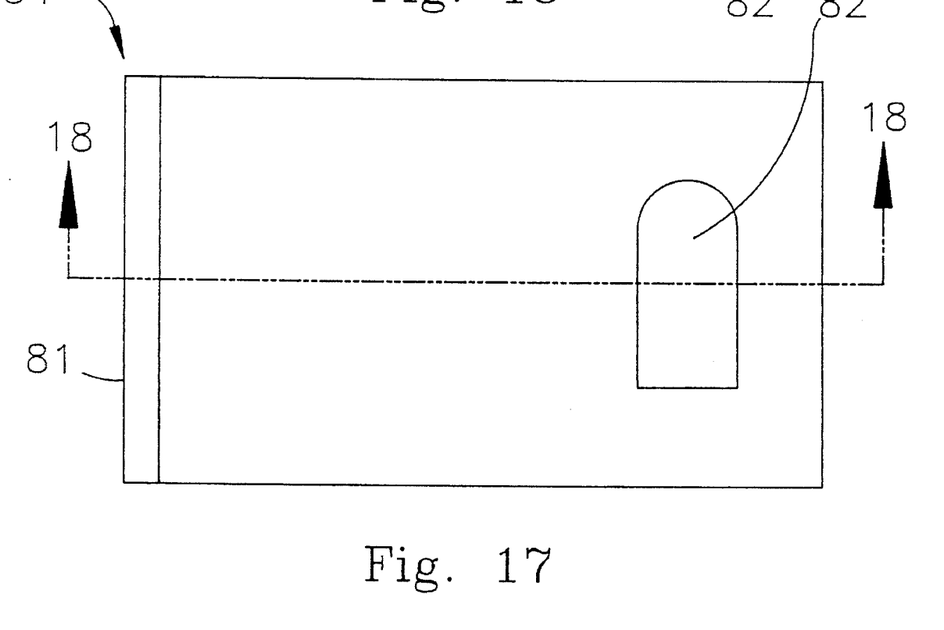
FIG. 17 is a top plan view of the knife of the present invention.
Figures 18, 19:
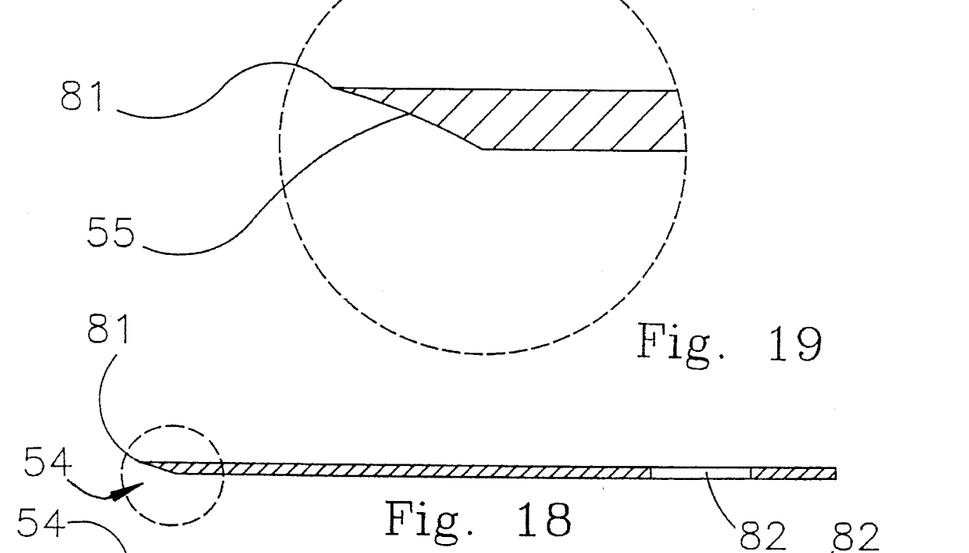
FIG. 18 is a section view along the line 18—18 of FIG. 17.
FIG. 19 is a blow-up of the circled portion of FIG. 18.

Shown in FIGS. 17–19 is the knife 54 having concave 55 edge 81 which is movable transverse the eye 50 to cut only the corneal tissue 51 under the inserts 48, 65 or 66 and, in particular, only the corneal tissue 51 under the corrected surface portions 46, 67 or 68. The knife extends in the recess 80 sufficiently in advance of the superstructure of drive mechanism 116, 114, 113, 111 which drives and advances the knife whereby the only portion of the device which passes over the eye during the cutting operation is the knife 54. The knife 54 has lug opening 82 therein, as more fully described below.

Knife 54 is preferably made of stainless steel.

3. The First Insert Holder and Motor Brace

Figure 20:
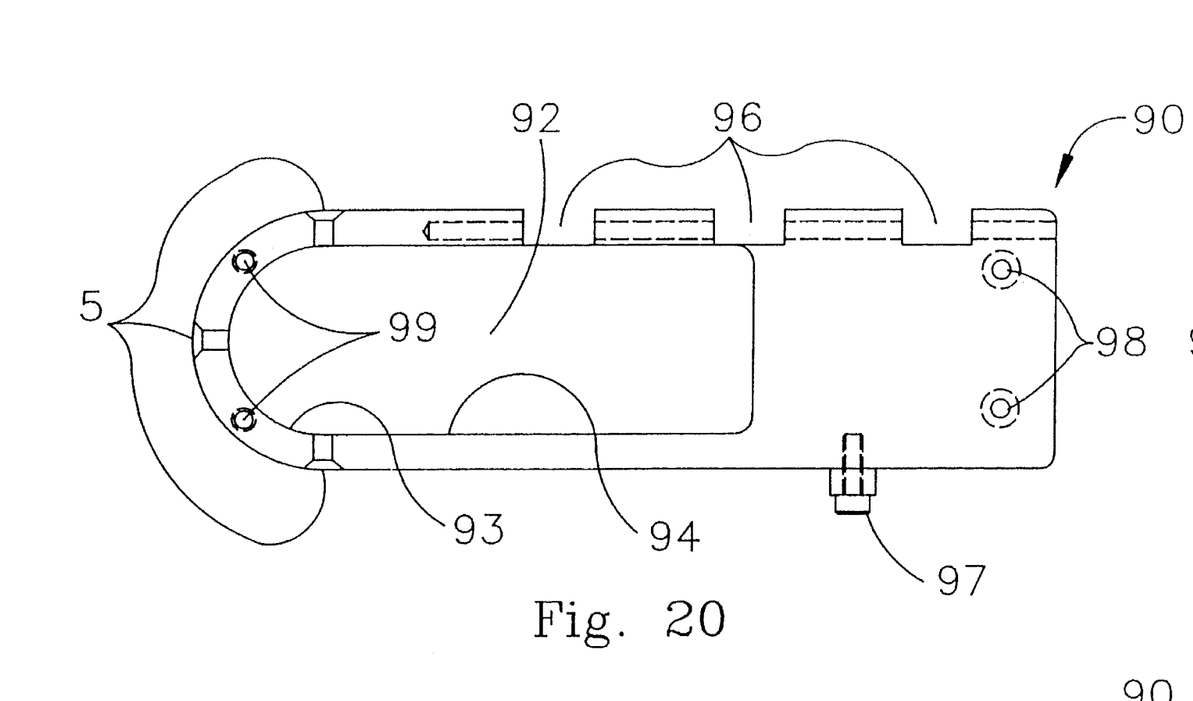
FIG. 20 is a top plan view of FIG. 21.
Figure 21:
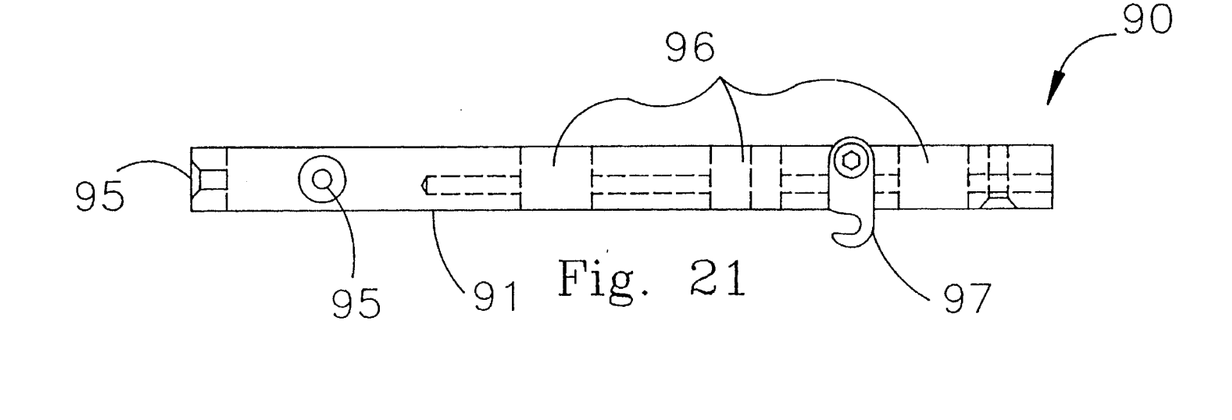
FIG. 21 is a front elevation of the first insert holder and motor brace of the present invention.
Figure 22:
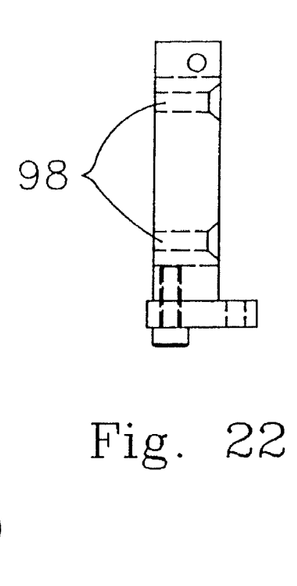
FIG. 22 is an end elevation view of FIG. 20.

Shown in FIGS. 20–21 is the first insert holder 90 having a planar surface 91 adjacent the suction ring recess 80. The planar surface 91 is non-adjustable relative to the recess 80 and has an opening 92 for receiving and holding the insert 48, 65 or 66, the face 47 of the insert, except for the corrected surface portion 46, 67 or 68 lying in the planar surface 91 with the knife edge 81 being contiguous the planar surface 91 and being guided by a bottom surface 82 (FIG. 15) of the recess 80 and the planar surface 91.

Figures 26, 27, 28:
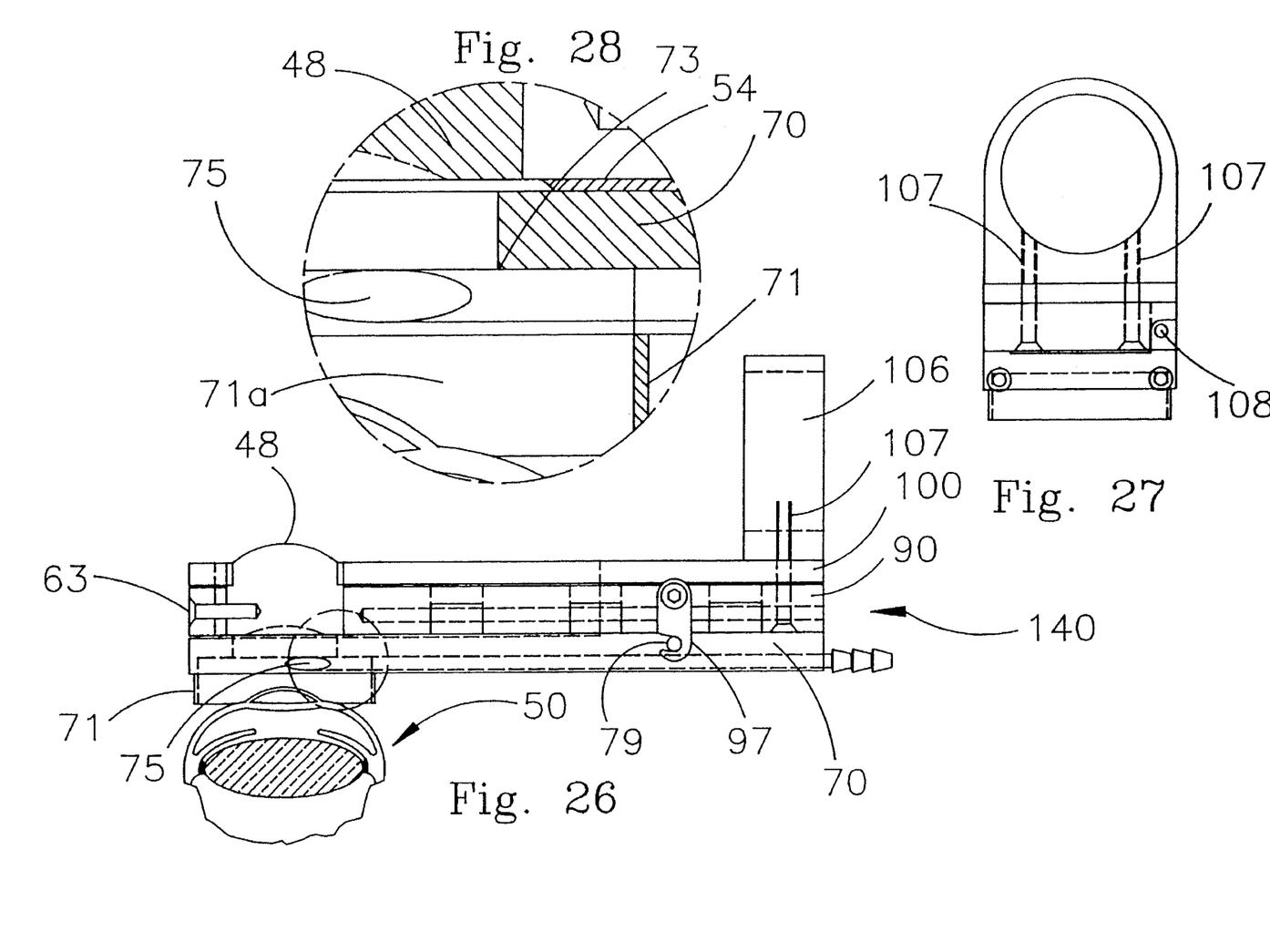
FIG. 26 is front elevation of the holder suction ring assembly of the present invention with insert and a schematic of the eye to which the assembly is to be applied.
FIG. 27 is a side elevation of FIG. 26.
FIG. 28 is a sectional blow-up of the circled portion of FIG. 26 in partial section along the line 28—28 of FIG. 14.

The opening 92 in insert holder 90 has left (as viewed in FIGS. 20,26) inner wall portion 93 touching a first (left) portion 60a (FIG. 12) of the outer surface 60 of the insert 48 adjacent the knife 54 and inner wall portions 94 (as seen in FIGS. 20, 26) which are open to the atmosphere relative to a second (right) portion 60b (FIG. 12) of the outer surface 60 of the insert 48 adjacent the knife (See FIG. 28). The first and second portions 60a, 60b are each substantially half of the outer surface of the insert adjacent the knife. The holders 90,100, insert 48 and suction ring and blade guide 70 form a single assembly 140. Note that ports 75 exit at the upper portion of the inner surface of ring 71, an area not contacted by the inserted sclera 52. Thus, the suction ring 71 and the sclera 52 of an eye 50 when received therein form a single and sole annular vacuum chamber 71a (FIG. 28) in the assembly between the holder 90 and insert 48, on the one hand, and the eye 50, on the other hand, and coupled 75, 74, 76, 131 to a vacuum source 133 for holding the assembly 140, 110 against the sclera 50 (FIGS. 26, 29) during the operation.

The vacuum at port 75 is adjustable by knob 132 allowing the surgeon to view the cornea 51 under the insert 48 and preferrably adjust the vacuum to the precise point where the cornea 51 only contacts the corrected portion 46 of insert 48 at the time of the cut. The same is true of the other corrected inserts.

Holes 95 in first holder 90 are registration holes and receive pins or screws to secure insert 48 in recess 92 of holder 90 indexing the corrected surface 46 to the position it had relative to the eye when the correction was prescribed and ground therein.

Recesses 96 are part of the hinge mechanism and with a hinge pin 108 (FIG. 27) rotatably receive hinge posts 77 to form an internal hinge. Clasp 97 releases suction ring and blade guide member 70 allowing it to swing open downwardly as seen in FIGS. 15, 21. Thus, the suction ring 71 is coupled to the insert holder 90 for inserting and removing the cutting blade and the insert 48 from the first holder 90, or for removing the cut disk 56 from between the upper surface of the knife 54 and the corrected surface 46 of an inserted insert 48 after an operation is performed, and the knife 54 is retracted.

4. The Second Insert Holder And Motor Brace

Figure 23:
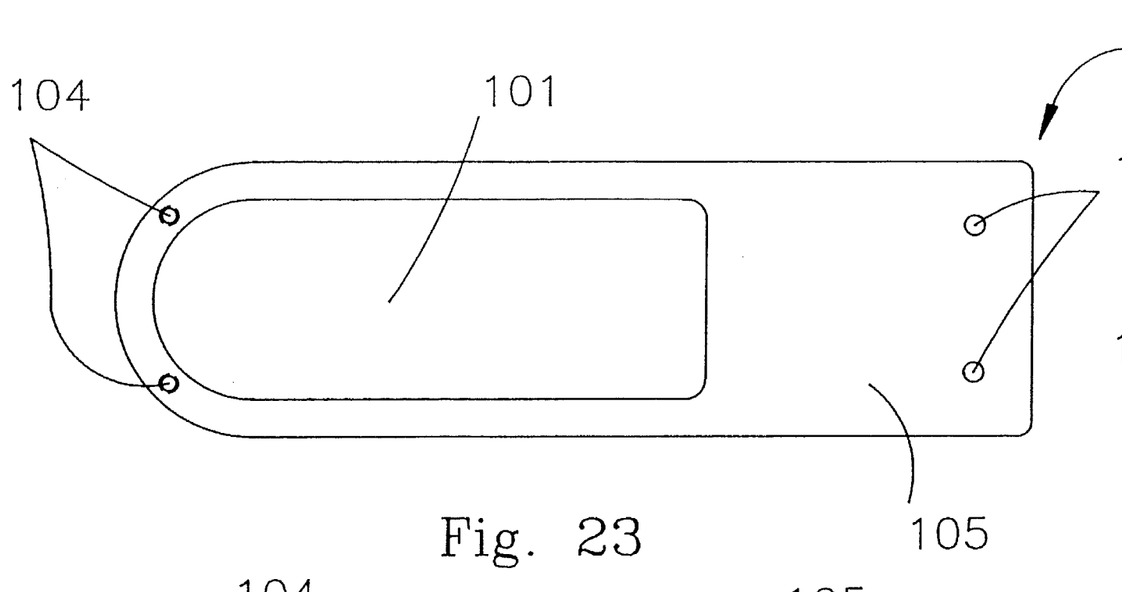
FIG. 23 is a top plan view of FIG. 24.
Figure 24:
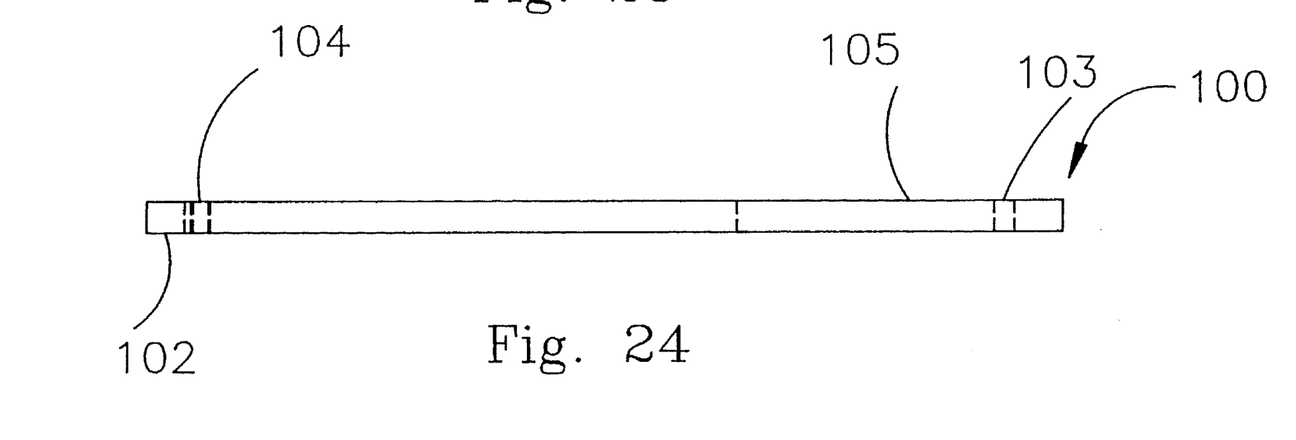
FIG. 24 is a front elevation view of the second insert holder and motor brace of the present invention.
Figure 25:
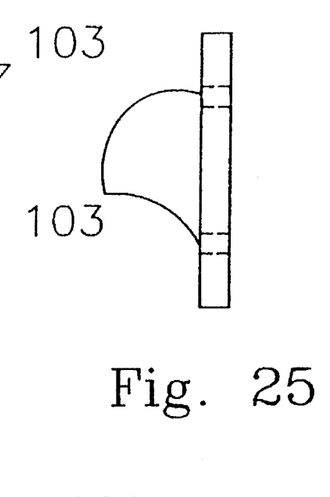
FIG. 25 is a side elevation of FIG. 23.

Shown in FIGS. 23–25 is the second insert holder and motor brace 100. As best seen in FIG. 26, however, the first insert holder 90 positioned adjacent the suction ring and blade guide 70, the second insert holder 100 positioned adjacent the first insert holder 90, and the insert 48 receivable and holdable between the first and second holder together form a unitary 140. Opening 101 in holder 100 is of smaller width than recess 92 in holder 90. The shoulder 62 of insert 48 abuts against the bottom surface 102 of holder 100 retaining the insert 48 in the first holder 90. Holders 90, 100 are held together by screws (not shown) in holes 99, 104 in holders 90, 100 and screws 107 in holes 98, 103 in holder 90, 100, respectively.

Attached to the upper surface 105 of the second holder 100 is motor bracket 106 (FIGS. 26,27) via screws 107 in holes 98,103. The bracket 106 is attached to a surface 105 of the holder 100 away from the suction ring and fixedly holds the housing 112 within which the electro-mechanical advancer 111 and motor 113 is slidably mounted for moving the knife 54 between retracted and advanced positions at a predetermined rate, as described more fully below.

The entire holder assembly 140, including suction ring and blade guide 70, holders 90, 100 and bracket 107 are preferably made of titanium alloy.

The Automated Advancer

Figures 29, 30:
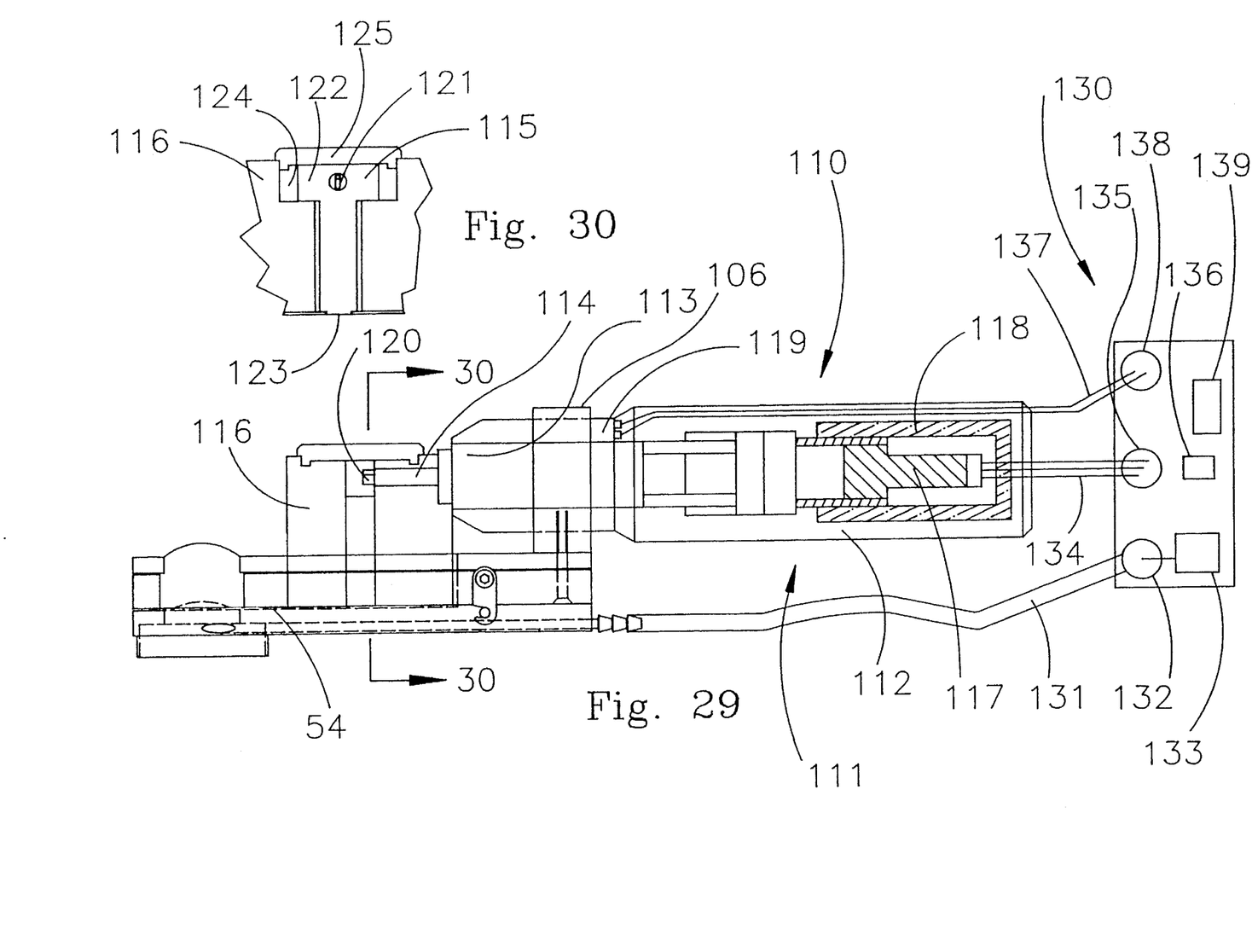
FIG. 29 is a front elevation in partial section of the complete assembly of the present invention including the drive and advance mechanisms and control console.
FIG. 30 is a sectional view along the line 30—30 of FIG. 29.

Shown in FIGS. 29,30 is the complete assembly 110 of the present invention. In particular is shown an electro-mechanical advancer 111 slidably mounted within a housing 112 and coupled to the knife 54 through motor 113 (slidably mounted within housing 112), shaft 114, T-cam 115 and cam block 116. The housing 112 may be either a unitary housing or a dual piece held together by clamps (not shown). The electro-mechanical advancer is a voice coil actuator. As is well known to those skilled in that art, due to the field of permanent magnet 118, the axial force generated upon coil 117 when current flows through the coil 117 produces relative motion between the field assembly and the coil 117. The lateral linear force pushes leftward (as seen in FIG. 29) the motor 113 within its housing 119, the shaft 114, the block 116 and the knife 54, advancing the knife to make the cut. The rate of advance is a function of the current in the coil of the actuator 111. Applicant has found voice coil actuators to be satisfactory. Applicant has found standard variable speed motors to be satisfactory.

The Drive Motor and Linear to Rotary Converter

Shown in FIGS. 29,30 is the drive motor 113, the shaft 114, the eccentric 120, the cam slot 121, the T-shaped cam 122, the cam lug 123, the T-shaped slot 124 and the screw cap 125. The rotatable shaft 114 is driven by the motor 113 in housing 112 fixedly mounted to the bracket 106. The eccentric extension 120 is at one end of the shaft.

The cam block 116 is frictionally mounted within openings 92, 101 of the holders 90, 100 with its bottom surface co-planar with the bottom surface 91 of holder 90 with lug 123 extending down into cam lug slot 82 of knife 54. Cam block 116 has T-shaped slot 124 mutually perpendicular to the axis of rotation of the shaft 114 and the plane of reciprocation of the knife 54 and is fixed relative to knife. The T-shaped cam 122 has cam slot 121 therein also mutually perpendicular to a axis of rotation of the shaft and a plane of reciprocation of the knife. The T-cam 122 is slidably reciprocably mounted in the T-slot 124. The eccentric extension 120 is slidably and rotatably received within the cam slot 121 whereby rotation of the shaft 114 is translated to reciprocation of the knife edge 81.

The Console

Shown in FIG. 29 is the console 130 with vacuum line 131 connected to vacuum control knob 132 and vacuum source 133, coil wires 134 connected to current control knob 135 and a power source 136, and motor wires 137 connected to motor control 138.

Also shown is a logic board 139 which can provide a variety of functions.

The console 130 has the following features: variable vacuum of 18–25" HG. with the suction ring affixed to the cornea: adjustable vacuum with bar indicator; automatic alarm and shutoff if the vacuum falls below a set amount; automatic release of vacuum after the drive motor moves 11 mm.; 24 v. vacuum pump controlled to maintain exact vacuum as desired; electrical input 120 v./60 cycles or European 210 automatically; variable rpm of the blade drive motor from 5000–30,000 rpm; digital indication of the rpm; automatic shutoff after drive motor moves 11 mm.; retract and reset drive motor to original position; and alarm or disfunction of drive motors if not in reset position.

Operation

The entire operation is very short and simple. The physician places the custom made insert 48 into the cutting instrument 110. He then places the insert 48, which is made of a clear material, over the cornea. He centers the insert on the exact center of the optical zone and activates the partial vacuum 132. He then activates the drive knob 138 which turns on the blade motor, and he activates the coil control knob 135 which automatically advances the blade drive 11 mm. When the blade advances to the 11 mm. point, the motor 113 and advancer 111 are automatically turned off and the partial vacuum 131 is released. The entire procedure from centering of the optical zone to the completion of the cut should take no more than 10 seconds. A patch is placed over the patient's eye and the operation is complete.

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed:

1. A surgical device for making a surgical cut to the cornea of an eye, said device comprising:

a base, said base comprising a single vacuum chamber adapted to engage the sclera of an eye, said vacuum chamber being connectable to a vacuum source;

an insert, said insert being carried on said base, said insert having a face disposed toward said eye, said face having a surface portion shaped according to a predetermined correction, said vacuum chamber being disposed around said insert, said insert not forming part of said vacuum chamber, and whereby application of vacuum to said vacuum chamber causes the cornea of said eye to engage said surface portion;

a knife having a knife edge, said knife being movable in a plane transverse to said face and adjacent to said face;

said base and said insert being cooperatively shaped such that said knife edge will cut only corneal tissue of said eye directly underneath said surface portion;

a drive device coupled to said knife edge for moving said knife, said drive device being operable such that only said knife and not said drive device is movable across said insert.

2. A surgical device in accordance with claim 1 wherein:
said insert is transparent.

3. A surgical device in accordance with claim 1 wherein:
said insert comprises a crosshair image, said crosshair image being disposed in alignment with said surface portion for aligning said insert with said eye.

4. A surgical device in accordance with claim 3 wherein:
said crosshair image includes scale markings.

5. A surgical device in accordance with claim 1 wherein:
said vacuum chamber comprises a suction ring said suction ring being coupleable to said vacuum source such that application of vacuum to said suction ring urges said eye into contact with said suction ring whereby the inner ocular pressure in said eye is increased thereby forcing the cornea of said eye against said shaped surface portion.

6. A surgical device in accordance with claim 1 wherein:
said base includes a portion for retaining said insert in registered alignment with said base.

7. A surgical device in accordance with claim 6 wherein:
said insert is transparent.

8. A surgical device in accordance with claim 7 wherein:
said insert comprises scale markings, said scale markings being used to align said insert over said eye.

9. A surgical device in accordance with claim 1 further comprising:

a controller, said controller being coupled to said drive device for controlling operation of said drive device by controlling application of energy to said drive device.

10. A surgical device in accordance with claim 9 wherein:
said controller is operable to apply energy to said drive device such that said knife edge is advanced to a predetermined position.

11. A surgical device in accordance with claim 10 wherein:
said controller is operable to apply energy to said drive device to advance said knife edge at a predetermined rate.

12. A surgical device in accordance with claim 1 comprising:
at least one vacuum passage in communication at one end with said vacuum chamber and connectable at its other end to said vacuum source.

13. A surgical device in accordance with claim 1 wherein:
said base includes a first registering portion; and
said insert includes a second registering portion, said first registering portion being adapted to engage said second registering portion whereby said insert is maintained on said base in a predetermined position.

14. A surgical device in accordance with claim 13 wherein:
said insert comprises transparent material.

15. A surgical device in accordance with claim 14 wherein:
said insert comprises visible alignment markings disposed on one surface thereof and in alignment with said shaped surface portion.

16. A surgical device in accordance with claim 14 wherein:
said insert comprises of acrylic plastic.

17. A surgical device in accordance with claim 16, wherein:
said acrylic plastic is polymethymethacrylate.

18. A surgical device in accordance with claim 1 wherein:
said drive device comprises a first drive device and a second drive device, said first drive device being adapted to move said knife edge across said insert, and said second drive device being adapted to oscillate said knife edge laterally with respect to said insert.

19. A surgical device in accordance with claim 1 wherein:
said knife edge has its cutting end shaped such that the top surface of said knife edge is flat and the bottom surface of said knife edge includes a concave portion.

20. A surgical device comprising:

a base, said base comprising a suction ring, said suction ring being adapted to engage the sclera of an eye to form a vacuum chamber with said eye;

an insert, said insert being carried on said base, said insert having a face disposed toward said eye, said face having a surface portion formed according to a predetermined correction;

a knife having a knife edge, said knife being movable in a plane transverse to and adjacent said face in said vacuum chamber;

a drive device for moving said knife, said drive device being selectively operable such that only said knife is movable across said insert, said insert being stationary relative to said base;

said suction ring is adapted to be coupled to a vacuum source whereby application of vacuum to said vacuum chamber from said vacuum source raises the inner ocular pressure of said eye thereby causing the cornea of said eye to be urged into contact with said surface portion; and whereby actuation of said drive device after said eye is urged into contact with said surface portion causes said knife edge to engage and cut said cornea only under said surface portion.

21. A device in accordance with claim 20 wherein:

said base comprises a portion for receiving said insert and retaining said insert in registered alignment with said base.

22. A surgical device in accordance with claim 21 wherein:

said insert is transparent.

23. A surgical device in accordance with claim 22 wherein:

said insert comprises alignment markings thereon for aligning said surgical device over an eye.

24. A surgical system for corrective surgical procedures on an eye, said system comprising:

a vacuum source;

a controller coupled to said vacuum source to control operation thereof;

a surgical device, said surgical device comprising:

a base, said base having a suction ring coupleable to said vacuum source and adapted to engage the sclera of an eye, such that said suction ring and said eye form a vacuum chamber;

an insert, said insert being carried on said base, said insert having a face disposed toward said eye, said face having a surface portion shaped according to a predetermined correction, said surface portion being surrounded by a flat circumferential portion;

a knife having a knife edge, said knife being movable in a plane transverse to said flat circumferential portion of said face and adjacent to said face such that said knife edge will cut only corneal tissue of said eye directly underneath said surface portion;

a drive device coupled to said knife for moving said knife in said plane, said drive device being operable such that only said knife is movable across said insert, said insert being stationary relative to said base; and said controller being coupled to said drive device and adapted to selectively energize said drive device whereby said drive device operates to move said knife across said insert to cut corneal tissue.

25. A system in accordance with claim 24 wherein:

said controller is operable to energize said drive device such that said drive device advances said knife edge a predetermined distance across said insert.

26. A system in accordance with claim 24 wherein:

said controller is adapted to control said vacuum source to maintain a predetermined vacuum level in said vacuum chamber.

27. An insert for use in a surgical device for altering the curvature of an eye, said surgical device comprising a base portion, said base portion comprising a suction ring and a portion adapted to receive said insert, said suction ring cooperating with the eye to form a vacuum chamber, said surgical device further comprising a drive device and a knife movable by said drive device in a plane immediately below and adjacent said insert, said insert comprising:

a member having top and bottom faces, said bottom face having a surface portion shaped in accordance with a predetermined desired correction, said shaped surface portion being surrounded by a flat circumferential portion, said member including at least one portion adapted to engage a corresponding second portion on said base whereby said insert will be carried on said base in predetermined alignment with said base.

28. An insert in accordance with claim 27 wherein:

said insert is formed of transparent material.

29. An insert in accordance with claim 27 wherein:

said transparent material is an acrylic plastic.

30. An insert in accordance with claim 27 wherein:

said insert comprises a top surface portion said top surface portion having alignment markings thereon.

31. An insert in accordance with claim 27, comprising:

a first portion adapted to engage said base to prevent rotational movement of said insert relative to said base.

32. An insert in accordance with claim 31 comprising:

a second portion adapted to engage said base to prevent and movement of said insert relative to said base.

33. An insert in accordance with claim 27 wherein:

said surface portion is shaped equivalent to a lenticular cut of said predetermined desired correction.

34. An insert in accordance with claim 27 wherein:

said predetermined desired correction corrects for surface irregularities of the cornea.

35. An insert in accordance with claim 27 wherein:

said predetermined desired correction is a prescriptive correction for astigmatism.

36. An insert in accordance with claim 27 wherein:

said predetermined desired correction is a prescriptive correction for myopia.

37. An insert in accordance with claim 27 wherein:

said predetermined desired correction is a prescriptive correction for hyperopia.

38. An insert for use in a surgical device for altering the curvature of an eye, said surgical device comprising a base portion, said base portion including a suction ring and a portion adapted to receive said insert, said suction ring cooperating with the eye to form a vacuum chamber, said surgical device further comprising a drive device and a knife movable by said drive device in a plane immediately below and adjacent said insert, said insert comprising:

a generally cylindrical member having top and bottom faces, said bottom face having a surface portion shaped in accordance with a predetermined desired correction, said member comprising a shoulder adapted to engage a surface of said device, and a first registering portion adapted to engage a first corresponding registering portion carried by said device whereby said insert is carried on said device in a predetermined alignment.

39. An insert in accordance with claim 38 wherein:

said insert is formed of transparent material.

40. An insert in accordance with claim 38 wherein:

said insert has a top surface portion, said top surface portion comprising alignment markings thereon.

41. An insert in accordance with claim 38, wherein:

said at least one registering portion comprises a first portion adapted to engage said base to prevent rotational movement of said insert relative to said base.

42. An insert in accordance with claim 41 comprising:

a second portion adapted to engage said base to prevent axial movement of said insert relative to said base.

43. An insert in accordance with claim 38 wherein:

said surface portion is shaped to be the equivalent of a lenticular cut of said predetermined desired correction.

44. An insert in accordance with claim 38 wherein:

said predetermined desired correction is a prescriptive correction for surface irregularities of said cornea.

45. An insert in accordance with claim 38 wherein:

said predetermined desired correction is a prescriptive correction for astigmatism.

46. An insert in accordance with claim 38 wherein:

said predetermined desired correction is a prescriptive correction for myopia.

47. An insert in accordance with claim 38 wherein:

said predetermined desired correction is a prescriptive correction for hyperopia.

48. An insert in accordance with claim 38 comprising:

a second registering portion adapted to engage a second corresponding registering portion carried on said device.

49. An insert in accordance with claim 38 wherein:

said first registering portion comprises a recess and said first corresponding registering portion comprises a protruding member.

50. A method of performing corrective eye surgery comprising the steps of:

determining a desired prescriptive correction for an eye;

determining a surface shape to be removed from the cornea of said eye from said correction;

forming an equivalent of said surface shape in a face of an insert to be used in a surgical device of a type which comprises a base, a suction ring carried by said base, a portion adapted to receive said insert, a knife carried on said base adjacent said insert, and a drive device coupled to said knife and operable to move said knife under said insert to cut said eye, said drive device being stationary with respect to said base and said insert;

inserting said insert in said surgical device;

placing said device over the eye to be corrected; and operating said device to perform a surgical cut on the cornea of said eye to produce said prescriptive correction directly to said eye.

\* \* \* \* \*